(12) United States Patent
Bittner et al.

(10) Patent No.: US 7,595,291 B2
(45) Date of Patent: Sep. 29, 2009

(54) ESTERIFIED ALKYL ALKOXYLATES USED AS LOW-FOAM SURFACTANTS

(75) Inventors: Christian Bittner, Mannheim (DE); Jürgen Tropsch, Römerberg (DE); Ralf Nörenberg, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/908,432

(22) PCT Filed: Mar. 10, 2006

(86) PCT No.: PCT/EP2006/060613

§ 371 (c)(1),
(2), (4) Date: Sep. 12, 2007

(87) PCT Pub. No.: WO2006/097435

PCT Pub. Date: Sep. 21, 2006

(65) Prior Publication Data

US 2008/0167215 A1    Jul. 10, 2008

(30) Foreign Application Priority Data

Mar. 14, 2005 (DE) .................. 10 2005 011608

(51) Int. Cl.
*C11D 1/72* (2006.01)
*C11D 1/74* (2006.01)
*C07C 69/24* (2006.01)

(52) U.S. Cl. .................. 510/360; 510/421; 510/475; 510/505; 510/535

(58) Field of Classification Search .................. 510/360, 510/421, 475, 505, 535
See application file for complete search history.

(56) References Cited

U.S. PATENT DOCUMENTS 4,088,598 A    5/1978    Williams

FOREIGN PATENT DOCUMENTS

| DE | 1243312 | | 6/1967 |
|---|---|---|---|
| DE | 2544707 | | 4/1976 |
| EP | 0035702 A2 | | 9/1981 |
| EP | 783012 | * | 7/1997 |
| WO | WO-94/03251 A1 | | 2/1994 |

OTHER PUBLICATIONS

Szymanowski, J., et al., "Synthesis and properties of esterification products of some oxyethylated alcohols and alkylphenols with fatty acids", Feite Seifen Anstrichmittel, 1980, vol. 82, No. 6, pp. 244-249, Jun. 1980.

* cited by examiner

*Primary Examiner*—Brian P Mruk
(74) *Attorney, Agent, or Firm*—Connolly Bove Lodge & Hutz LLP

(57) ABSTRACT

The present invention relates to low-foam surfactant mixtures of the general formula (I)

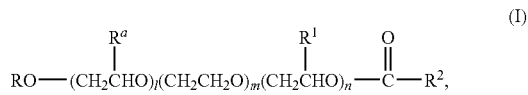

where R, $R^a$, $R^1$ and $R^2$, l, n and m have the meaning given in the description and the claims, and to the production thereof. For example, $R=C_{13}$-alkyl, $R^a=H$, l=5, m=22, n=1, $R^1$=methyl and $R^2=C_6$-$C_{14}$-alkyl. The surfactants are suitable for detergent and cleaner formulations.

10 Claims, No Drawings

ESTERIFIED ALKYL ALKOXYLATES USED AS LOW-FOAM SURFACTANTS

The present invention relates to low-foam surfactant mixtures, and to the production thereof. The surfactants are suitable for detergent and cleaner formulations.

Surfactants are substances which can lower the interfacial tension. Typically, surfactants have a characteristic structure and have at least one hydrophilic and at least one hydrophobic functional group. If both parts of the molecule are in equilibrium relative to one another, the substance will accumulate and orient itself at an interface, i.e. hydrophilic groups point, for example, to an aqueous phase and the hydrophobic groups in the direction of other solid, liquid or gaseous phases. A further special feature of the surfactants is the formation of higher aggregates, the so-called micelles. With these, the surfactant molecules arrange themselves in such a way that the polar groups form, for example, a spherical shell. This has the effect of solubilizing substances such as dirt particles in an aqueous solution with the formation of micelles.

Surfactants are therefore particularly suitable for the cleaning of surfaces and as an additive in detergents.

Surfactants which have one hydrophobic constituent and one hydrophilic constituent are widespread. However, their tendency toward foaming renders them unusable or only usable to a limited extent for many applications. For this reason, nonionic surfactants in particular have been proposed which have a second hydrophobic block so that the foam volume is limited.

DE-A 12 43 312 describes, for example, the use of alkyl alkoxylates which are esterified with an aliphatic short-chain or aromatic carboxylic acid as low-foam nonionic surfactants.

Similar compounds are disclosed in DE-A 25 44 707. Here too, the acid component is formed by a short-chain aliphatic acid, namely acetic acid.

EP-A 035 702 discloses foam suppressants which comprise nonionic surfactants. These surfactants reportedly include 3 to 10 ethylene oxide units.

WO-A 94/03251 discloses terminally capped antifoams in which the alcohol component used is a fatty alcohol polyglycol ether which likewise preferably comprises up to 10 ethylene oxide or propylene oxide units.

A common aspect of the known nonionic surfactants is that their foam-suppressing properties are accompanied with only moderate washing and cleaning properties. In particular, the ability to be formulated in alkaline conditions can be problematic for low-chain surfactants.

The object of the present invention is therefore to provide low-foam, in particular solid, surfactants whose foam formation is at least comparable with that of known surfactants and which have improved washing and/or cleaning power.

The object is achieved by a low-foam surfactant mixture comprising compounds of the general formula (I)

(I)

where

R is a branched or unbranched alkyl radical having 8 to 16 carbon atoms;

$R^a$, $R^1$ independently of one another, are hydrogen or a branched or unbranched alkyl radical having 1 to 5 carbon atoms;

$R^2$ is an unbranched alkyl radical having 5 to 17 carbon atoms;

l, n independently of one another, are a number from 1 to 5 and m is a number from 13 to 35.

It has namely been found that the surfactant mixtures, despite their high HLB value, can have surprisingly excellent foam suppression coupled with good wetting ability preferably in a temperature range from 0 to 120° C.

The HLB value is given here as the quotient of the amount of ethylene oxide to the total amount×20. The HLB value is generally defined by the formula $$HLB = 20\left(1 - \frac{M_L}{M_G}\right),$$

where $M_L$ is the molecular weight of the lipophilic fractions and $M_G$ is the total weight. Further details on this can be found in H.-D. Dörfer, Grenzflächen und kolloid-disperse Systeme [Interfaces and colloidally disperse systems], Springer Verlag 2002, chapter 9.3 "Physikalische Eigenschaften und Wirkungen der Tenside" [Physical properties and effects of surfactants].

It has also been found that the surfactant mixtures according to the invention can also be stable in the alkaline area of application. This makes it possible to formulate them in alkaline cleaners.

In addition, it is found that the surfactant mixtures according to the invention can be present in the solid state at room temperature. As a result of this, they can be used more easily in solid detergent or cleaner formulations.

It is likewise found that the surfactants according to the invention, particularly when the glycol unit with which the acid component is esterified is other than ethylene glycol, can have long-term stability. This is particularly advantageous for operations which require a certain minimum time, for example, during the washing operation Preferred surfactant mixtures according to the present invention comprise compounds of the general formula (II)

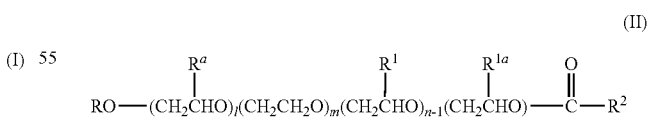

(II)

where $R^{1a}$ is a branched or unbranched alkyl radical having 1 to 5 carbon atoms and R, $R^a$, $R^1$, $R^2$, l, m and n have the above meaning.

For the purposes of the present invention, the expression "alkyl radical" means a saturated branched or unbranched aliphatic hydrocarbon radical with the number of carbon atoms stated in each case.

In addition, the surfactant mixtures of the present invention can additionally comprise compounds of the formula (III),

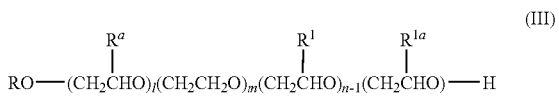

In this case, the polyalcohol is present in its unesterified form. However, the molar ratio of ester (I) to alcohol (III) is preferably at least 1:1, more preferably at least 2:1 and most preferably at least 3:1.

It is also preferred that at least 50%, preferably at least 75% and more preferably at least 90%, of the compounds in the surfactant mixture according to the invention are compounds of the formula (I), (II) or (III).

Preferably, the radical R is a branched alkyl radical having 9 to 16, more preferably having 10 to 13, carbon atoms. The degree of branching is preferably 1-3. For the purposes of the present invention, the term "degree of branching" is understood as meaning the number of methyl groups reduced by 1.

Further preferably, $R^a$, $R^1$ independently of one another, are hydrogen, methyl and ethyl. If $R^a$, $R^1$ occur more frequently, then each can be chosen independently of a further $R^a$ or $R^1$. Thus $R^a$, $R^1$ can occur blockwise or in random distribution.

$R^{1a}$ is preferably methyl or ethyl.

$R^2$ is preferably a branched or unbranched alkyl radical having 5 to 13 carbon atoms.

Preferably n=1, l=5 and m is preferably a number from 13 to 34, more preferably 13 to 33, even more preferably 13 to 30, most preferably 17 to 27.

Further preferably, the average molecular weight is in a range from 950 to 2300 g/mol. Particularly preferably, the average molecular weight is in a range from 1200 to 1900 g/mol.

Preferably more than 50% of the compounds of the surfactant mixture according to the present invention are compounds of the formula (II) or compounds of the formula (I), where, in the compounds of the formula (I), at least one $R^1$ is not hydrogen.

Preferably, the surfactant mixture has a start of the melting range above 25° C. More preferably, the value is above 30° C.

The present invention further provides the production of surfactant mixtures comprising the steps:

a) reaction of an alcohol of the formula ROH with an epoxide of the formula

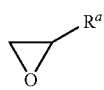

and then with ethylene oxide;

b) reaction of the product from step a) with an epoxide of the formula

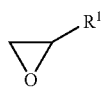

and optionally with an epoxide of the formula

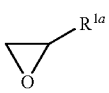

c) reaction of the product formed from step b) with a carboxylic acid $R^2$—COOH or a methyl ester $R^2$—COOCH$_3$, where $R^1$, $R^{1a}$ and $R^2$ have the meaning as in claim 1 or 2.

If, in step a), $R^a$=H, the reaction is carried out only with ethylene oxide.

Steps a) and b) preferably take place by anhydrous base-catalyzed reaction. The base used here is preferably sodium hydroxide or potassium hydroxide. The temperature range is preferably 50 to 200° C.

The reaction in step c) is preferably carried out with acid or base catalysis; the acid used is preferably sulfuric acid or paratoluenesulfonic acid. The temperature range in step c) can be from 80 to 200° C. Preferably, the reaction step c) takes place with the continuous removal of the water of reaction or methanol. This is carried out, for example, at atmospheric pressure and/or stripping with nitrogen or reduced pressure or by using an entrainer, such as, for example, toluene or xylene, in the case of water.

The surfactant mixtures according to the invention are particularly suitable in detergent and cleaner formulations. The invention therefore further provides a detergent or cleaner formulation comprising a surfactant mixture according to the invention.

The surfactant mixtures are particularly preferably used in so-called "2 in 1" or "3 in 1" tabs. Further details on these formulations is given in Hermann G. Hauthal, G. Wagner (Ed.), Reinigungs- und Pflegemittel im Haushalt [Domestic cleaning and care compositions], Verlag für chemische Industrie, H. Ziolkowsky GmbH, Augsburg 2003, chapter 4.2, pages 161-184.

For the purposes of this invention, detergents generally serve for the washing of materials of greater or lesser flexibility preferably those which comprise or consist of natural, synthetic or semisynthetic fiber materials and which consequently usually have at least partially a textile character. The materials which comprise or consist of fibers can, in principle, be in any form which exists in use or for production and processing. For example, fibers may be unarranged in the form of staple or aggregate, arranged in the form of threads, yarns, twines, or in the form of fabrics, such as nonwovens, loden materials or felt, wovens, knits in all conceivable types of weave.

These may be raw fibers or fibers in any stages of processing and may be natural protein or cellulose fibers, such as wool, silk, cotton, sisal, hemp, coconut fibers or synthetic fibers, such as, for example, polyester, polyamide or polyacrylonitrile fibers.

The detergents according to the invention can also be used particularly advantageously in the course of processing fiber materials, e.g. for degreasing raw wool or for desizing fiber materials of all types.

The detergents according to the invention can also be used for cleaning fiber-containing materials, such as, for example, backed carpets with cut or uncut pile.

The cleaner according to the invention is particularly well suited for the cleaning of materials with a continuous, in particular hard, surface, i.e. of surfaces which have no or very few and small pores and consequently have no or only low absorption capacity.

Materials with continuous surfaces are predominantly hard, but can also be soft in the sense that they have a certain reversible or irreversible deformability.

Examples of materials with hard surfaces for whose cleaning the cleaners according to the invention are preferably used are metal, glass, enamel, ceramic. Typical objects made of these materials are, for example, metal sinks, cutlery, glass and porcelain crockery, bath tubs, wash basins, tiles and cured synthetic resins, such as, for example, decorative melamine resin surfaces on kitchen furniture or painted metal surfaces such as refrigerators and car bodies. The cleaners according to the invention are also very valuable auxiliaries in the production of printed circuits, where it is a question of removing traces of grease and other impurities from copper- or silver-coated substrates prior to engraving and/or prior to assembly, and/or for completely removing soldering pastes or other flux residues after assembly.

The cleaners according to the invention can also be useful during the manufacture of microchips. Materials with continuous, in particular hard, surfaces for the purposes of this invention can also have fissured surfaces, as are found, for example, with cermets.

Examples of softer materials which can be cleaned using the cleaners according to the invention are, for example, sealed or painted woods, e.g.; parquet or wall paneling, window frames, doors, plastic coverings such as floor coverings made of PVC or hard rubber, or rigid or flexible foams having largely continuous surfaces.

In particular, the cleaners according to the invention can, for example, be used as hand dishwashing detergents, machine dishwashing detergents, metal degreasers, glass cleaners, floor cleaners, all-purpose cleaners, high-pressure cleaners, neutral cleaners, alkaline cleaners, acidic cleaners, spray degreasers, dairy cleaners, large-scale catering establishment cleaners, apparatus cleaners in industry, in particular the chemical industry, as cleaners for car washes, but also as household all-purpose cleaners.

The compositions of the detergents and cleaners are of course adapted to the various purposes, as is known to the person skilled in the art from the prior art. For this purpose, all auxiliaries and additives appropriate for the purpose and known from the abovementioned prior art can be added to the detergents and cleaners according to the invention.

In many cases, it is expedient to combine the surfactant mixtures of the formula (I) used according to the invention with other nonionic surfactants, such as, for example, alcohol alkoxylates, alkylamine alkoxylates, alkylamide alkoxylates, alkyl polyglucosides, or with ionic, preferably anionic, surfactants, such as, for example, longer-chain or long-chain alcohol sulfate/ether sulfates, alkylbenzenesulfonates, α-olefinsulfonates, sulfosuccinates, or with amphoteric surfactants, such as, for example, alkylamine oxides, or betaines.

Examples of surfactants of varying nature which are suitable for combination are given below:

Examples of suitable nonionic surfactants are alkoxylated $C_8$- to $C_{22}$-alcohols, such as fatty alcohol alkoxylates or oxo alcohol alkoxylates. The alkoxylation can be carried out with ethylene oxide, propylene oxide and/or butylene oxide. Surfactants which can be used here are all alkoxylated alcohols which preferably contain two added molecules of an abovementioned alkylene oxide. Also suitable here are block polymers of ethylene oxide, propylene oxide and/or butylene oxide, or addition products which contain said alkylene oxides in random distribution. 2 to 50 mol, preferably 3 to 20 mol, of at least one alkylene oxide is used per mole of alcohol. The alkylene oxide used is preferably ethylene oxide. The alcohols preferably have 10 to 18 carbon atoms. Alkoxylates with a broad or narrow alkylene oxide homolog distribution can be obtained depending on the type of alkoxylation catalyst.

A further class of suitable nonionic surfactants are alkylphenol alkoxylates, such as alkylphenol ethoxylates having $C_6$ to $C_{14}$-alkyl chains and 5 to 30 mol of alkylene oxide units.

Another class of nonionic surfactants are alkyl polyglucosides having 6 to 22, preferably 8 to 18, carbon atoms in the alkyl chain. These compounds mostly contain 1 to 20, preferably 1.1 to 5, glucoside units.

Another class of nonionic surfactants are N-alkylglucamides of the general structures

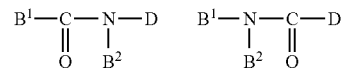

where $B^1$ is a $C_6$- to $C_{22}$-alkyl, $B^2$ is hydrogen or $C_1$- to C4-alkyl and D is a polyhydroxyalkyl radical having 5 to 12 carbon atoms and at least 3 hydroxyl groups. Preferably, $B^1$ is $C_{10}$- to $C_{18}$-alkyl, $B^2$ is $CH_3$ and D is a $C_5$ or $C_6$ radical. Such compounds are obtained, for example, by the acylation of reductively aminated sugars with acid chlorides of $C_{10}$- to $C_{18}$-carboxylic acids.

Further suitable nonionic surfactants are the terminally capped fatty acid amide alkoxylates known from WO-A 95/11225 and of the general formula

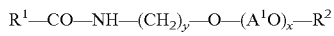

in which
$R^1$ is a $C_5$- to $C_{21}$-alkyl or alkenyl radical,
$R^2$ is a $C_1$- to $C_4$-alkyl group,
$A^1$ is a $C_2$- to $C_4$-alkylene,
y is the number 2 or 3 and
x has a value from 1 to 6.

Examples of such compounds are the reaction products of n-butyltriglycolamine of the formula $H_2N$—$(CH_2$—$CH_2$—$O)_3$—$C_4H_9$ with methyl dodecanoate, or the reaction products of ethyltetraglycolamine of the formula $H_2N$—$(CH_2$—$CH2$—$O)_4$—$C_2H_5$ with a commercially available mixture of saturated $C_8$- to $C_{18}$-fatty acid methyl esters.

Further suitable nonionic surfactants are also block copolymers of ethylene oxide, propylene oxide and/or butylene oxide (Pluronic® and Tetronic® grades from BASF), polyhydroxy or polyalkoxy fatty acid derivatives, such as polyhydroxy fatty acid amides, N-alkoxy- or N-aryloxypolyhydroxy fatty acid amides, fatty acid amide ethoxylates, in particular those which are terminally capped, and fatty acid alkanolamide alkoxylates.

The additional nonionic surfactants are preferably present in the detergents and cleaners according to the invention in an amount of from 0.01 to 30% by weight, in particular 0.1 to 25% by weight, especially 0.5 to 20% by weight.

It is possible to use individual nonionic surfactants or a combination of different nonionic surfactants. It is possible to use nonionic surfactants from just one class, in particular only alkoxylated $C_8$- to $C_{22}$-alcohols, but it is also possible to use surfactant mixtures from different classes.

Suitable anionic surfactants are, for example, fatty alcohol sulfates of fatty alcohols having 8 to 22, preferably 10 to 18, carbon atoms, e.g. $C_9$-$C_{11}$-alcohol sulfates, $C_{12}$-$C_{14}$-alcohol sulfates, $C_{12}$-$C_{18}$-alcohol sulfates, lauryl sulfate, cetyl sulfate, myristyl sulfate, palmityl sulfate, stearyl sulfate and tallow fatty alcohol sulfate.

Further suitable anionic surfactants are sulfated ethoxylated $C_8$-$C_{22}$-alcohols (alkyl ether sulfates) or soluble salts thereof Compounds of this type are prepared, for example, by firstly alkoxylating a $C_8$- to $C_{22}$-alcohol, preferably a $C_{10}$-$C_{18}$-alcohol, e.g. a fatty alcohol, and then sulfating the alkoxylation product. For the alkoxylation, preference is given to using ethylene oxide, 1 to 50 mol, preferably 1 to 20 mol, of ethylene oxide being used per mole of alcohol. The alkoxylation of the alcohols can, however, also be carried out with propylene oxide alone and optionally butylene oxide. Also suitable are those alkoxylated $C_8$-$C_{22}$-alcohols which contain ethylene oxide and propylene oxide or ethylene oxide and butylene oxide or ethylene oxide and propylene oxide and butylene oxide. The alkoxylated $C_8$-$C_{22}$-alcohols can contain the ethylene oxide, propylene oxide and butylene oxide units in the form of blocks or in random distribution. It is possible to obtain alkyl ether sulfates having a broad or narrow alkylene oxide homolog distribution depending on the type of alkoxylation catalyst.

Further suitable anionic surfactants are alkanesulfonates, such as $C_8$-$C_{24}$-alkanesulfonates, preferably $C_{10}$-$C_{18}$-alkanesulfonates, and soaps, for example the Na and K salts of $C_8$- to $C_{24}$-carboxylic acids.

Further suitable anionic surfactants are linear $C_8$-$C_{20}$-alkylbenzenesulfonates ("LAS"), preferably linear $C_9$-$C_{13}$-alkylbenzenesulfonates and -alkyltoluenesulfonates.

Further suitable anionic surfactants are also $C_8$- to $C_{24}$-olefinsulfonates and -disulfonates, which can also be mixtures of alkene- and hydroxyalkanesulfonates or -disulfonates, alkyl ester sulfonates, sulfonated polycarboxylic acids, alkylglycerol sulfonates, fatty acid glycerol ester sulfonates, alkylphenol polyglycol ether sulfates, paraffinsulfonates having about 20 to about 50 carbon atoms (based on paraffin recovered from natural sources, or on paraffin mixtures), alkylphosphates, acylisethionates, acyltaurates, acylmethyltaurates, alkylsuccinic acids, alkenyisuccinic acids or monoesters or monoamides thereof, alkylsulfosuccinic acids or amides thereof, mono- and diesters of sulfosuccinic acids, acylsarcosinates, sulfated alkylpolyglucosides, alkylpolyglycolcarboxylates and hydroxyalkylsarcosinates.

The anionic surfactants are preferably added in the form of salts to the detergent and cleaner. Suitable cations in these salts are alkali metal ions such as sodium, potassium and lithium and ammonium salts, such as, for example, hydroxyethylammonium, di(hydroxyethyl)ammonium and tri(hydroxyethyl)ammonium salts. The anionic surfactants are present in the detergents according to the invention preferably in an amount of up to 30% by weight, for example from 0.1 to 30% by weight, especially 1 to 25% by weight, in particular 3 to 20% by weight. If $C_9$-$C_{20}$ linear alkylbenzenesulfonates (LAS) are co-used, these are usually used in an amount up to 15% by weight, in particular up to 10% by weight.

The anionic surfactants are present in the cleaners according to the invention in an amount of up to 30% by weight, especially up to 25% by weight, in particular up to 15% by weight. If $C_9$-$C_{20}$-linear-alkylbenzenesulfonates (LAS) are co-used, these are usually used in an amount up to 10% by weight, in particular up to 8% by weight.

It is possible to use individual anionic surfactants or a combination of different anionic surfactants. It is possible to use anionic surfactants from only one class, for example only fatty alcohol sulfates or only alkylbenzenesulfonates, although it is also possible to use surfactant mixtures from different classes, e.g. a mixture of fatty alcohol sulfates and alkylbenzenesulfonates.

Also, the surfactant mixtures of the formula I to be used according to the invention can be combined with cationic surfactants, usually in an amount up to 25% by weight, preferably 0.1 to 15% by weight, for example $C_8$-$C_{16}$-dialkyldimethylammonium halides, dialkoxydimethylammonium halides or imidazolinium salts with a long-chain alkyl radical; and/or with amphoteric surfactants, usually in an amount up to 15% by weight, preferably 0.1 to 10% by weight, for example derivatives of secondary or tertiary amines, such as $C_6$-$C_{18}$-alkylbetaines or $C_6$-$C_{15}$-alkylsulfobetaines or amine oxides, such as alkyldimethylamine oxides.

The surfactant mixtures of the formula (I) to be used according to the invention are usually combined with builders (sequestering agents), such as polyphosphates, polycarboxylates, phosphonates, complexing agents, e.g. methylglycinediacetic acid and salts thereof, nitrilotriacetic acid and salts thereof, ethylenediaminetetraacetic acid and salts thereof, and optionally with cobuilders.

Individual builder substances which are highly suitable for combination with the surfactants of the formula (I) to be used according to the invention may be listed below:

Suitable inorganic builders are primarily crystalline or amorphous alumosilicates having ion-exchange properties, such as, in particular, zeolites. Different types of zeolites are suitable, in particular zeolites A, X, B, P, MAP and HS in their Na form or in forms in which Na is partially exchanged for other cations, such as Li, K, Ca, Mg or ammonium. Suitable zeolites are described, for example, in U.S. Pat. No. 4,604,224.

Crystalline silicates which are suitable as builders are, for example, disilicates or phyllosilicates, e.g. δ-$Na_2Si_2O_5$ or β-$Na_2Si_2O_5$ (SKS 6 or SKS 7 respectively). The silicates can be used in the form of their alkali metal, alkaline earth metal or ammonium salts, preferably as Na, Li and Mg silicates. Amorphous silicates, such as, for example, sodium metasilicate, which has a polymeric structure, or amorphous disilicate (Britesil® H 20 manufacturer: Akzo) can likewise be used.

Suitable inorganic carbonate-based builder substances are carbonates and hydrogencarbonates. These can be used in the form of their alkali metal, alkaline earth metal or ammonium salts Preference is given to using Na, Li and Mg carbonates or hydrogen carbonates, in particular sodium carbonate and/or sodium hydrogencarbonate. Customary phosphates used as inorganic builders are alkali metal orthophosphates and/or polyphosphates, such as pentasodium triphosphate. Said builder components can be used individually or in mixtures with one another.

In addition, in many cases it is expedient to add cobuilders to the detergents and cleaners according to the invention. Examples of suitable substances are listed below:

In a preferred embodiment, the detergents and cleaners according to the invention comprise, in addition to the inorganic builders, 0.05 to 20% by weight, in particular 1 to 10% by weight, of organic cobuilders in the form of low molecular weight, oligomeric or polymeric carboxylic acids, in particular polycarboxylic acids, or phosphonic acids or salts thereof, in particular Na or K salts.

Examples of low molecular weight carboxylic acids or phosphonic acids which are suitable as organic cobuilders are:

Phosphonic acids, such as 1-hydroxyethane-1,1-diphosphonic acid, aminotris(methylenephosphonic acid), ethylenediaminetetra(methylenephosphonic acid), hexamethylenediaminetetra(methylenephosphonic acid) and diethylenetriaminepenta(methylenephosphonic acid); $C_4$-$C_{20}$-di-, -tri- and -tetracarboxylic acids, such as succinic acid, propanetricarboxylic acid, butanetetracarboxylic acid, cyclopentanetetracarboxylic acid and alkyl- and alkenylsuccinic acids having $C_2$-$C_{16}$-alkyl or alkenyl radicals respectively; $C_4$-$C_{20}$-hydroxycarboxylic acids, such as malic acid, tartaric acid, gluconic acid, glutaric acid, citric acid, lactobionic acid and sucrosemono-, di- and tri-carboxylic acid; aminopolycarboxylic acids, such as nitrilotriacetic acid, β-alaninediacetic acid, ethylenediaminetetraacetic acid, serinediacetic acid, isoserinediacetic acid, alkyl ethylenediaminetriacetate, N,N-bis(carboxymethyl)glutamic acid, ethylenediaminedisuccinic acid and N-(2-hydroxyethyl)iminodiacetic acid, methyl- and ethylglycinediacetic acid.

Examples of oligomeric or polymeric carboxylic acids which are suitable as organic cobuilders are:

Oligomaleic acids, as described, for example, in EP-A 451508 and EP-A 396303; co- and terpolymers of unsaturated $C_4$-$C_8$-dicarboxylic acids, the copolymerized comonomers being monoethylenically unsaturated monomers from group (i), given below, in amounts of up to 95% by weight, from group (ii) in amounts of up to 60% by weight and from group (iii) in amounts of up to 20% by weight.

Examples of unsaturated $C_4$- to $C_8$-dicarboxylic acids in this context are maleic acid, fumaric acid, itaconic acid and citraconic acid. Preference is given to maleic acid.

Group (i) includes monoethylenically unsaturated $C3$-$C_8$-monocarboxylic acids, such as acrylic acid, methacrylic acid, crotonic acid and vinylacetic acid. From group (i), preference is given to using acrylic acid and methacrylic acid.

Group (ii) includes monoethylenically unsaturated $C_2$-$C_{22}$-olefins, vinyl alkyl ethers having $C_1$-$C_8$-alkyl groups, styrene, vinyl esters of $C_1$-$C_8$-carboxylic acids, (meth)acrylamide and vinylpyrrolidone. From group (ii), preference is given to using $C_2$-$C_8$-olefins, vinyl alkyl ethers having $C_1$-$C_4$-alkyl groups, vinyl acetate and vinyl propionate.

If the polymers of group (ii) contain copolymerized vinyl esters, some or all of the latter can also be present in hydrolyzed form to give vinyl alcohol structural units Suitable co- and terpolymers are known, for example, from U.S. Pat. No. 3,887,806 and DE-A 4313909.

Group (iii) includes (meth)acrylic esters of $C_1$-$C_8$-alcohols, (meth)acrylonitrile, (meth)acrylamides of $C_1$-$C_8$-amines, N-vinylformamide and N-vinylimidazole.

Also suitable as organic cobuilders are homopolymers of monoethylenically unsaturated $C_3$-$C_8$-monocarboxylic acids, such as acrylic acid, methacrylic acid, crotonic acid and vinylacetic acid, in particular acrylic acid and methacrylic acid, copolymers of dicarboxylic acids, such as copolymers of maleic acid and acrylic acid in the weight ratio 10:90 to 95:5, particularly preferably those in the weight ratio 30:70 to 90:10 having molar masses of from 1000 to 150,000;

terpolymers of maleic acid, acrylic acid and a vinyl ester of a $C_1$-$C_3$-carboxylic acid in the weight ratio 10 (maleic acid):90 (acrylic acid+vinyl ester) to 95 (maleic acid):10 (acrylic acid+vinyl ester), where the weight ratio of acrylic acid to the vinyl ester can vary within the range from 30:70 to 70:30;

copolymers of maleic acid with $C_2$-$C_8$-olefins in the molar ratio 40:60 to 80:20, copolymers of maleic acid with ethylene, propylene or isobutene in the molar ratio 50:50 being particularly preferred.

Graft polymers of unsaturated carboxylic acids onto low molecular weight carbohydrates or hydrogenated carbohydrates, cf. U.S. Pat. No. 5,227,446, DE-A 4415623 and DE-A 4313909, are likewise suitable as organic cobuilders.

Examples of suitable unsaturated carboxylic acids in this context are maleic acid, fumaric acid, itaconic acid, citraconic acid, acrylic acid, methacrylic acid, crotonic acid and vinylacetic acid, and mixtures of acrylic acid and maleic acid, which are grafted on in amounts of from 40 to 95% by weight, based on the component to be grafted.

For modification, it is additionally possible for up to 30% by weight, based on the component to be grafted, of further monoethylenically unsaturated monomers to be present in copolymerized form. Suitable modifying monomers are the abovementioned monomers of groups (ii) and (iii).

Suitable graft bases are degraded polysaccharides, such as acidically or enzymatically degraded starches, inulins or cellulose, protein hydrolysates and reduced (hydrogenated or reductively aminated) degraded polysaccharides, such as mannitol, sorbitol, aminosorbitol and N-alkylglucamine, and also polyalkylene glycols having molar masses up to $M_w$=5000, such as polyethylene glycols, ethylene oxide/propylene oxide or ethylene oxide/butylene oxide or ethylene oxide/propylene oxide/butylene oxide block copolymers and alkoxylated mono- or polyhydric $C_1$- to $C_{22}$-alcohols (cf. U.S. Pat. No. 5,756,456).

Polyglyoxylic acids suitable as organic cobuilders are described, for example, in EP-B-001004, U.S. Pat. No. 5,399,286, DE-A-4106355 and EP-A-656914. The end groups of the polyglyoxylic acids can have different structures.

Polyamidocarboxylic acids and modified polyamidocarboxylic acids suitable as organic cobuilders are known, for example, from EP-A-454126, EP-B-511037, WO-A-94/01486 and EP-A-581452.

In particular, polyaspartic acids or cocondensates of aspartic acid with further amino acids, $C_4$-$C_{25}$-mono- or -dicarboxylic acids and/or $C_4$-$C_{25}$-mono- or -diamines are also used as organic cobuilders. Particular preference is given to using polyaspartic acids which have been prepared in phosphorus-containing acids and modified with $C_6$-$C_{22}$-mono- or -dicarboxylic acids or with $C_6$-$C_{22}$-mono- or -diamines.

Also suitable as organic cobuilders are iminodisuccinic acid, oxydisuccinic acid, aminopolycarboxylates, alkylpolyaminocarboxylates, aminopolyalkylenephosphonates, polyglutamates, hydrophobically modified citric acid, such as agaric acid, poly-α-hydroxyacrylic acid, N-acyl ethylenediaminetriacetates, such as lauroyl ethylenediaminetriacetate, and alkylamides of ethylenediaminetetraacetic acid, such as EDTA-tallow amide.

Furthermore, it is also possible to use oxidized starches as organic cobuilders.

In a further preferred embodiment, the cleaners according to the invention additionally comprise, in particular in addition to the inorganic builders, the anionic surfactants and/or the nonionic surfactants, 0.5 to 20% by weight, in particular 1 to 10% by weight, of glycine-N,N-diacetic acid derivatives, as described in WO 97/19159.

It is also frequently expedient to add bleaching systems, consisting of bleaches, such as perborate, percarbonate, and optionally bleach activators, such as tetraacetylethylenediamine, +bleach stabilizers to the detergents and cleaners according to the invention.

In these cases, the detergents and cleaners according to the invention additionally comprise 0.5 to 30% by weight, in particular 5 to 27% by weight, especially 10 to 23% by weight, of bleaches in the form of percarboxylic acids, e.g. diperoxododecanedicarboxylic acid, phthalimidopercaproic acid or monoperoxophthalic acid or -terephthalic acid, adducts of hydrogen peroxide with inorganic salts, e.g. sodium perborate monohydrate, sodium perborate tetrahydrate, sodium carbonate perhydrate or sodium phosphate perhydrate, adducts of hydrogen peroxide with organic compounds, e.g. urea perhydrate, or of inorganic peroxo salts, e.g. alkali metal persulfates or -peroxodisulfates, optionally in combination with 0 to 15% by weight, preferably 0.1 to 15% by weight, in particular 0.5 to 8% by weight, of bleach activators.

Suitable bleach activators are:
polyacylated sugars, e.g. pentaacetylglucose;
acyloxybenzenesulfonic acids and alkali metal and alkaline earth metal salts thereof, e.g. sodium p-nonanoyloxybenzenesulfonate or sodium p-benzoyl-oxybenzenesulfonate;

N,N-diacylated and N,N,N',N'-tetraacylated amines, e.g. N,N,N',N'-tetraacetylmethylenediamine and -ethylenediamine (TAED), N,N-diacetylaniline, N,N-diacetyl-p-toluidine or 1,3-diacylated hydantoins, such as 1,3-diacetyl-5,5-dimethylhydantoin;

N-alkyl-N-sulfonylcarbonamides, e.g. N-methyl-N-mesylacetamide or N-methyl-N-mesylbenzamide;

N-acylated cyclic hydrazides, acylated triazoles or urazoles, e.g. monoacetylmaleic hydrazide;

O,N,N-trisubstituted hydroxylamines, e.g. O-benzoyl-N,N-succinylhydroxylamine, O-acetyl-N,N-succinylhydroxylamine or O,N,N-triacetylhydroxylamine;

N,N'-diacylsulfurylamides, e.g. N,N'-dimethyl-N,N'-diacetylsulfurylamide or N,N'-diethyl-N,N'-dipropionylsulfurylamide;

acylated lactams, for example acetylcaprolactam, octanoylcaprolactam, benzoylcaprolactam or carbonylbiscaprolactam;

anthranil derivatives, such as 2-methylanthranil or 2-phenylanthranil;

triacyl cyanurates, e.g. triacetyl cyanurate or tribenzoyl cyanurate;

oxime esters and bisoxime esters, such as O-acetylacetone oxime or bisisopropyl-iminocarbonate;

carboxylic anhydrides, e.g. acetic anhydride, benzoic anhydride, m-chlorobenzoic anhydride or phthalic anhydride;

enol esters, such as isopropenyl acetate;

1,3-diacyl-4,5-diacyloxyimidazolines, e.g. 1,3-diacetyl-4,5-diacetoxyimidazoline;

tetraacetylglycoluril and tetrapropionylglycoluril;

diacylated 2,5-diketopiperazines, e.g. 1,4-diacetyl-2,5-diketopiperazine;

ammonium-substituted nitriles, such as N-methylmorpholinium acetonitrile methylsulfate;

acylation products of propylene diurea and 2,2-dimethylpropylenediurea, e.g. tetraacetylpropylenediurea;

α-acyloxypolyacylmalonamides, e.g. α-acetoxy-N,N'-diacetylmalonamide;

diacyidioxohexahydro-1,3,5-triazines, e.g. 1,5-diacetyl-2,4-dioxohexahydro-1,3,5-triazine;

benz-(4H)-1,3-oxazin-4-ones having alkyl radicals, e.g. methyl, or aromatic radicals, e.g. phenyl, in the 2-position.

The described bleaching system comprising bleaches and bleach activators can optionally also comprise bleach catalysts. Examples of suitable bleach catalysts are the quaternized imines and sulfonimines which are described, for example, in U.S. Pat. No. 5,360,569 and EP-A 453 003. Particularly effective bleach catalysts are manganese complexes, which are described, for example, in WO-A 94/21777. Where used, such compounds are incorporated into the detergents and cleaners in amounts of at most 1.5% by weight, in particular up to 0.5% by weight, and in the case of very active manganese complexes, in amounts up to 0.1% by weight.

In addition to the described bleaching system comprising bleaches, bleach activators and optionally bleach catalysts, it is also possible to use systems having enzymatic peroxide release or photoactivated bleaching systems for the detergents and cleaners according to the invention.

For a number of uses, it is expedient for the detergents and cleaners according to the invention to comprise enzymes. Enzymes which are preferably used in detergents and cleaners are proteases, amylases, lipases and cellulases. Preferred amounts of the enzymes are from 0.1 to 1.5% by weight, particularly preferably 0.2 to 1.0% by weight, of the formulated enzyme. Examples of suitable proteases are Savinase and Esperase (manufacturer Novo Nordisk). An example of a suitable lipase is Lipolase (manufacturer: Novo Nordisk). An example of a suitable cellulase is Celluzym (manufacturer: Novo Nordisk). The use of peroxidases for activating the bleach system is also possible. It is possible to use individual enzymes or a combination of different enzymes. Where appropriate, the detergent and cleaner according to the invention can also comprise enzyme stabilizers, e.g. calcium propionate, sodium formate or boric acids or salts thereof, and/or antioxidants.

The constituents of detergents and cleaners are known in principle to the person skilled in the art. The lists, above and below, of suitable constituents give merely an illustrative selection of the known suitable constituents.

In addition to the main components stated hitherto, the detergents and cleaners according to the invention can also comprise the following further customary additives in the amounts customary for this purpose:

known dispersants, such as naphthalenesulfonic acid condensates or polycarboxylates, pH-regulating compounds, such as alkalis or alkali donors (NaOH, KOH, pentasodium metasilicate) and acids (hydrochloric acid, phosphoric acid, amidosulfuric acid, citric acid), buffer systems, such as acetate or phosphate buffer, perfume, dyes, biocides, such as isothiazolinones or 2-bromo-2-nitro-1,3-propanediol, solubilizers/hydrotropic agents, such as cumenesulfonates, toluenesulfonates, short-chain fatty acids, urea, alcohols or phosphoric alkyl/aryl esters, alkyl/aryl polyglycol phosphoric esters, foam regulators for stabilizing or suppressing foam, skin protectants and corrosion inhibitors, disinfecting compounds or systems, such as those which liberate chlorine or hypochlorous acid, such as dichlorolsocyanurate, or which comprise iodine.

The detergents additionally comprise, if appropriate, soil carriers, soil release agents, such as, for example, polyether esters, incrustation inhibitors, ion exchangers, graying inhibitors, optical (fluorescent) whiteners, color transfer inhibitors, such as, for example, polyvinylpyrrolidone, thickeners and extenders and formulating agents, in cleaners solvents such as, for example, short-chain alkyl oligoglycols, such as butyl glycol, butyl diglycol, propylene glycol monomethyl ether, alcohols, such as ethanol, isopropanol, aromatic solvents such as toluene, xylene, N-alkylpyrrolidones or alkylene carbonates, thickeners, such as, for example, polysaccharides, and/or weakly crosslinked polycarboxylates (for example Carbopol® from Goodrich), finely divided abrasive components, such as, for example, quartz or marble powder, chalk, diatomaceous earth, pumice or else crocus or emery, may additionally be present.

The detergents are usually, but not exclusively, in solid, pulverulent form, and then generally additionally comprise customary extenders, which impart to them good flowability, dosability and solubility and which prevent agglomeration and dusting, such as, for example, sodium sulfate or magnesium sulfate. In the conventional form, the pulverulent detergents have an average bulk density of about 450 g/l. Compact or ultracompact detergents and also extrudates have a bulk density of >600 g/l. These are becoming more and more important.

If they are used in liquid form, they can be in the form of aqueous microemulsions, emulsions or solutions. In liquid detergents, solvents such as, for example, ethanol, isopropanol, 1,2-propylene glycol, or butyl glycol can additionally be used.

In the case of gel-like detergents according to the invention, thickeners, such as, for example, polysaccharides and/or weakly crosslinked polycarboxylates (for example Carbopol® from Goodrich) can additionally be used.

In the case of detergents in tablet form, tableting auxiliaries, such as, for example, polyethylene glycols with molar masses of >1000 g/mol, polymer dispersions, and tablet disintegrants, such as, for example, cellulose derivatives, crosslinked polyvinylpyrrolidone, crosslinked polyacrylates or combinations of acids, e.g. citric acid+sodium bicarbonate, to name but a few, are additionally required.

The cleaners are usually, but not exclusively, aqueous and are in the form of microemulsions, emulsions or solutions.

If they are to be in solid or pulverulent form, customary extenders, which impart to them good flowability, dosability and solubility and/or which prevent agglomeration and dusting, such as, for example, sodium sulfate or magnesium sulfate, can additionally be used.

In the case of cleaners in tablet form, tableting auxiliaries, such as, for example, polyethylene glycols with molar masses >1000 g/mol, polymer dispersions, and tablet disintegrants, such as, for example, cellulose derivatives, crosslinked polyvinylpyrrolidone, crosslinked polyacrylates or combinations of acids, e.g. citric acid+sodium bicarbonate, to name but a few, are additionally required.

The present invention will be illustrated in more detail by reference to the examples below.

EXAMPLES

Example 1

Tridecylpentacosaoxyethylene Glycol C8-C18-Coconut Fatty Acid Ester (Hydrogenated) (A)

a) Preparation of the Alkyl Alkoxylate:

Tridecanol N (160 g, 0.8 mol; manufacturer BASF) is admixed with powdered KOH (2 g, 0.036 mol) in a 2 l pressurized autoclave from Mettler and dewatered for 1 h at 95° C. and 20 mbar. The system is then rendered inert twice using nitrogen and heated to 100° C. Over the course of 8 h and up to a maximum pressure of 6 bar, ethylene oxide (880 g, 20 mol) is metered in and when the addition is complete, the mixture is after-stirred for a further 3 h. Finally, the compound is admixed with Ambosol (3 percent by weight) and filtered. This gives tridecylpentacosaoxyethylene glycol (1040 g; OH number 45 mg of KOH/g, theory 43.2 mg of KOH/g) as white solid.

b) Esterification:

Tridecylpentacosaoxyethylene glycol (149.5 g, 0.12 mol) is admixed with hydrogenated C8-C18-coconut fatty acid (24.8 g, 0.12 mol; Edenor HK 818, Cognis), paratoluenesulfonic acid (1.1 g, 0.06 mol) and toluene (50 ml) and boiled for 10 h at 140° C. at the water separator. This gives 170 g of solid (m.p.: 33° C.) with a degree of esterification of >95% $^1$H NMR.

*Typical composition of Edenor HK 18 according to manufacturer:

| Chain distribution | Specified limiting values | Typical values |
|---|---|---|
| C6 | 0-1 | traces |
| C8 | 2-10 | 6 |
| C10 | 4-8 | 6 |
| C12 | 45-55 | 49 |

-continued

| Chain distribution | Specified limiting values | Typical values |
|---|---|---|
| C14 | 17-21 | 19 |
| C16 | 7-13 | 10 |
| C18 | 7-14 | 10 |
| >C18 | 0-0.5 | traces |

Example 2

2-Propylheptylcosaoxyethylene Glycol Decanoic Ester (B)

a) Preparation of the Alkyl Alkoxylate:

2-Propylheptanol (158.3 g, 1.0 mol; manufacturer BASF) is admixed with powdered KOH (2.1 g, 0.038 mol) in a 2 l pressurized autoclave from Mettler and dewatered for 1 h at 95° C. and 20 mbar. The system is then rendered inert twice using nitrogen and heated to 100° C. Over the course of 8 h and up to a maximum pressure of 6 bar, ethylene oxide (880 g, 20 mol) is metered in and, when the addition is complete, the mixture is after-stirred for a further 3 h. Finally, the compound is mixed with Ambosol (3 percent by weight) and filtered. This gives 2-propylheptylcosaoxyethylene glycol (1035 g; OH number 54 mg of KOH/g, theory 55 mg of KOH/g) as white solid.

b) Esterification:

2-Propylheptylcosaoxyethylene glycol (124.6 g, 0.12 mol) is admixed with decanoic acid (20.7 g, 0.12 mol), paratoluenesulfonic acid (1.1 g, 0.06 mol) and toluene (50 ml) and boiled for 10 h at 140° C. at the water separator. This gives 140 g of solid (m.p.: 30° C.) with a degree of esterification of 93% ($^1$H-NMR).

Example 3

2-Propylheptyldecaoxyethylene Glycol Decanoic Ester (C, Prior Art)

Lutensol® XP 100 (168.8 g, 0.4 mol; BASF) is admixed with decanoic acid (68.8 g, 0.4 mol), paratoluenesulfonic acid (1.1 g, 0.06 mol) and toluene (50 ml) and boiled for 10 h at 140° C. at the water separator. This gives 230 g of liquid substance with a degree of esterification of 80% ($^1$H NMR)

Example 4

2-Propylheptylhexaoxyethylene Glycol Decanoic Ester (D, Prior Art)

Lutensol® XP 60 (101.3 g, 0.24 mol; BASF) is admixed with decanoic acid (49.6 g, 0.24 mol), paratoluenesulfonic acid (2.2 g, 0.12 mol) and toluene (50 ml) and boiled for 10 h at 140° C. at the water separator. This gives 140 g of liquid substance with a degree of esterification of 90% ($^1$H NMR)

Example 5

2-Propylheptyloxypropylenecosaoxyethylene Glycol Decanoic Ester (E)

a) Preparation of the Alkyl Alkoxylate:

2-Propylheptanol (395.8 g, 2.5 mol; manufacturer BASF) is admixed with powdered KOH (11 g, 0.20 mol) in a 3.5 l pressurized autoclave from Mettler and dewatered for 1 h at 95° C. and 20 mbar. The system is then rendered inert twice using nitrogen and heated to 120° C. Over the course of 1 h and up to a maximum pressure of 2 bar, propylene oxide (145 g, 2 mol) is metered in and the mixture is after-stirred for 2 h at constant pressure. Then, at 120° C., over the course of 8 h and up to a maximum pressure of 6 bar, ethylene oxide (880 g, 50 mol) is metered in and, when the addition is complete, the mixture is after-stirred for a further 3 h. Finally, the compound is admixed with Ambosol (3 percent by weight) and filtered. This gives 2-propylheptyloxypropylenecosaoxyethylene glycol (2744 g; OH number 52 mg of KOH/g, theory 51 mg of KOH/g) as white solid.

b) Esterification:

2-Propylheptyloxypropylenecosaoxyethylene glycol (165 g, 0.15 mol) is admixed with decanoic acid (25.8 g, 0.15 mol), paratoluenesulfonic acid (1.4 g, 0.075 mol) and toluene (50 ml) and boiled for 10 h at 140° C. at the water separator. This gives 189 g of solid with a degree of esterification of 82% ($^1$H NMR)

Example 6

2-Propylheptylcosaoxyethyleneoxyypropylene Glycol Decanoic Ester (F)

a) Preparation of the Alkyl Alkoxylate:

2-Propylheptanol (158.3 g, 1.0 mol; manufacturer BASF) is admixed with powdered KOH (4.4 g, 0.078 mol) in a 2 l pressurized autoclave from Mettler and dewatered for 1 h at 95° C. and 20 mbar. The system is then rendered inert twice using nitrogen and heated to 120° C. Over the course of 8 h and up to a maximum pressure of 8 bar, ethylene oxide (880 g, 20 mol) is metered in, and, when the addition is completed, the mixture is after-stirred for a further 6 h. The reactor is then decompressed to atmospheric pressure and, over the course of 2 h and up to a pressure of 7 bar, propylene oxide (58 g, 1 mol) is metered in at 120° C. Finally, the compound is admixed with Ambosol (3 percent by weight) and filtered. This gives 2-propylheptylcosaoxyethylene glycol (1030 g; OH number 54 mg of KOH/g, theory 51 mg of KOH/g) as white solid.

b) Esterification:

2-Propylheptylcosaoxyethyleneoxypropylene glycol (124.7 g, 0.12 mol) is admixed with decanoic acid (20.6 g, 0.12 mol), paratoluenesulfonic acid (1.1 g, 0.06 mol) and toluene (50 ml) and boiled for 10 h at 140° C. at the water separator. This gives 142 g of solid with a degree of esterification of 90% ($^1$H NMR)

Example 7

Tridecylheptacosaoxyethylene Monopropylene Glycol C6-C14-Carboxylic Acid Ester (G)

a) Preparation of the Alkyl Alkoxylate:

Tridecanol N (140 g, 0.7 mol; manufacturer BASF) is admixed with 50% strength aqueous KOH (4.4 g of aqueous solution, 0.039 mol) in a 2 l pressurized autoclave from Mettler and dewatered for 1 h at 95° C. and 20 mbar. The system is then rendered inert twice using nitrogen and heated to 120° C. Over the course of 12 h and up to a maximum pressure of 6 bar, ethylene oxide (832 g, 18.9 mol) is metered in, and after the addition is completed, the mixture is after-stirred for a further 2 h. The reactor is then decompressed to atmospheric pressure and, over the course of 2 h and up to a pressure of 7 bar, propylene oxide (40.6 g, 0.7 mol) is metered in at 120° C. and the mixture is after-stirred for 2 h. This gives tridecylheptacosaoxyethylene monopropylene glycol (1020 g; OH number 40 mg of KOH/g, theory 39 mg of KOH/g) as white solid.

b) Esterification:

Tridecylheptacosaoxyethylene monopropylene glycol (100 g, 0.071 mol) is boiled with C6C10-methyl ester (6.0 g, 0.036 mol; Edenor ME C6-10, Cognis*) and C12C14-methyl ester (7.8 g, 0.036 mol; Edenor ME C1270, Cognis*) and at 160° C. under a stream of N2 for 4 h. This gives 107 g of beige solid (m.p.: 33-35° C.) with a degree of esterification of 75% ($^1$H NMR). This can be converted into a white solid by adding H$_2$O$_2$ (3.3 g of a 30% strength in water) and stirring for 20 min at 60° C., and neutralization with acetic acid (0.23 g, 0.004 mol).

*Typical composition of Edenor ME C6-10 according to manufacturer:

| Chain distribution | Specified limiting values |
| --- | --- |
| C6 | 3-8 |
| C8 | 40-65 |
| C10 | 35-50 |
| C12 | 0-5 |

*Typical composition of Edenor ME C1270 according to manufacturer:

| Chain distribution | Specific limiting values |
| --- | --- |
| C10 | <2 |
| C12 | 70-75 |
| C14 | 22-30 |
| C16 | <2 |
| C18 | <0.5 |

Example 8

Foam Volume in the Dishwasher

The foam volume in the dishwasher is investigated For this, 10 ml of chicken egg, 19 g of a base dishwasher detergent (main constituents 48% sodium metasilicate×5H$_2$O, 45% sodium triphosphate, 5% sodium carbonate) and 1 g of the surfactant are placed in the dishwasher. The number of revolutions of the spray arm is then meaured at different temperatures. If the level of foam is too high, the speed of the spray arm is reduced by braking, and if the level is low it can be operated at maximum speed (about 150 rpm). Various surfactants were tested in this application.

| Name | Surfactant main component |
| --- | --- |
| A | C$_{13}$-alcohol-25 EO + hydrogenated coconut fatty acid (Cognis: Edenor HK 818) |
| B | 2-PH-20 EO + decanoic acid |
| C (prior art) | 2-PH-10 EO + decanoic acid |
| D (prior art) | 2-PH-6 EO + decanoic acid |
| E | 2-PH-1PO-20 EO + decanoic acid |
| F | 2-PH-20 EO-1 PO + decanoic acid |
| G | C$_{13}$-alcohol-27 EO-1 PO + C$_6$C$_{14}$-methyl ester |

The rotational speed was measured at 30, 40, 50, 60° C. The table below lists the rotor speeds in rpm at various temperatures.

| Temperature | A | B | C | D | E | F | G |
|---|---|---|---|---|---|---|---|
| 30° C. | 119 | 122 | 128 | 131 | 113 | 123 | 117 |
| 40° C. | 127 | 126 | 131 | 129 | 120 | 127 | 113 |
| 50° C. | 126 | 129 | 129 | 125 | 128 | 129 | 111 |
| 60° C. | 128 | 130 | 127 | 112 | 128 | 129 | 125 |

Example 9

Contact Angle on Hard Surfaces

The table below gives the contact angle of aqueous surfactant solutions (0.2 g/l) after 0.1 s, 1 s and 10 s in degrees at 40° C. on various hard surfaces. The smaller the angle, the more marked the wetting. Various surfactants were tested.

| Contact angle | A | B | C | D | E | F | G | Water |
|---|---|---|---|---|---|---|---|---|
| Glass | 39/35/23 | 43/40/29 | 44/41/33 | 36/34/28 | 41/37/24 | 35/32/20 | 43/36/29 | 45/42/41 |
| Steel | 62/62/48 | 65/61/50 | 68/67/61 | 70/70/68 | 61/60/46 | 63/62/49 | 51/44/32 | 82/78/78 |
| Polyethylene | 65/65/52 | 71/68/61 | 73/72/71 | 75/74/74 | 72/69/58 | 68/67/57 | 58/53/41 | 94/95/94 |

Example 10

Ability to be Formulated

The table below gives the ability to be formulated (1 g of surfactant per 49 g of cleaner solution) in two typical alkaline cleaner formulations. What is assessed is whether the surfactant dissolves in the cleaner formulations to form a clear solution. If the formulations are clear, then the cloud point is also determined (behavior at 20° C./cloud point in ° C.). Various surfactants were tested.

| Cleaner | A | B | C | D | E | F | G |
|---|---|---|---|---|---|---|---|
| pH 7.5 | clear/64 | clear/59 | cloudy/— | cloudy/— | clear/64 | clear/66 | not measured |
| pH 9.2 | clear/65 | clear/61 | cloudy/— | cloudy/— | clear/66 | clear/67 | clear/59 |

Example 11

Stability Tests Over the Application Range

The test takes place analogously to Example 8. The rotational speeds are measured at maximum temperature (60° C.-69° C.) over a period of 2 h.

| | Time [min] | | | | | | | | | | | |
|---|---|---|---|---|---|---|---|---|---|---|---|---|
| | 10 | 20 | 30 | 40 | 50 | 60 | 70 | 80 | 90 | 100 | 110 | 120 |
| E | 128 | 126 | 126 | 125 | 125 | 123 | 123 | 121 | 117 | 113 | 103 | 91 |
| F | 130 | 128 | 128 | 127 | 128 | 127 | 127 | 127 | 125 | 125 | 125 | 123 |

We claim:

1. A low-foam surfactant mixture comprising compounds of formula (I)

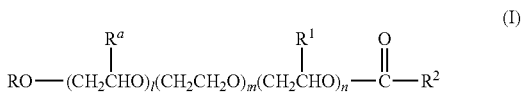

wherein

R is a branched or unbranched alkyl radical having 8 to 16 carbon atoms;

$R^a$ and $R^1$ are, independently of one another, hydrogen or a branched or unbranched alkyl radical having up to 5 carbon atoms;

$R^2$ is an unbranched alkyl radical having 5 to 17 carbon atoms;

l and n are, independently of one another, an integer from 1 to 5; and m is an integer from 17 to 27.

2. The surfactant mixture of claim 1, further comprising compounds of formula (II)

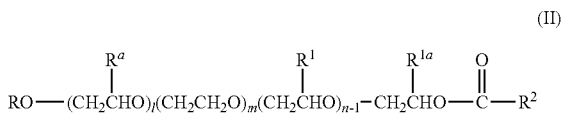

wherein $R^{1a}$ is a branched or unbranched alkyl radical having up to 5 carbon atoms.

3. The surfactant mixture of claim 1, wherein at least one of the following requirements is satisfied:

a) R is a branched alkyl radical having 10 to 13 carbon atoms;

b) $R^a$ and $R^1$ are, independently of one another, hydrogen, methyl, or ethyl;

c) $R^2$ is a branched or unbranched alkyl radical having 5 to 13 carbon atoms;

d) n is 1 and l is 5.

4. The surfactant mixture of claim 1, wherein the average molecular weight of said mixture is from 1200 g/mol to 1900 g/mol.

5. The surfactant mixture of claim 1, wherein the start of the melting range of said mixture is greater than 25° C.

6. The surfactant mixture of claim 2, wherein greater than 50% of said compounds are compounds of formula (II) or compounds of formula (I) wherein at least one $R^1$ is not hydrogen.

7. A method for producing the surfactant mixtures of claim 1, comprising:
   a) reaction of an alcohol of formula ROH with an epoxide of the formula (III)

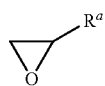

(III)

and then with ethylene oxide;
   b) reaction of the product of a) with an epoxide of formula (IV)

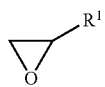

(IV)

and optionally with an epoxide of formula (V)

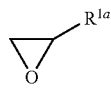

(V)

c) reaction of the product of b) with a carboxylic acid of formula $R^2$—COOH or a methyl ester of formula $R^2$—COOCH$_3$.

8. The method of claim 7, wherein at least one of the following conditions is satisfied:
   a) the reactions in a) and b) take place under anhydrous base catalysis;
   b) the temperatures in a) and b) take place in a temperature range of from 50 to 200° C.;
   c) the reaction in c) takes place under acid-base catalysis in the case of $R^2$—COOH or base catalysis in the case of $R^2$—COOCH$_3$;
   d) the temperature in c) takes place in a temperature range of from 80 to 200° C.;
   e) the reaction in c) takes place with the continuous removal of the water of reaction or methanol.

9. A detergent or cleaner formulation comprising the surfactant mixture of claim 1.

10. The surfactant mixture of claim 2, wherein $R^{1a}$ is methyl or ethyl.

\* \* \* \* \*